United States Patent [19]

Wandell

[11] Patent Number: Plant 6,745

[45] Date of Patent: Apr. 18, 1989

[54] LITTLELEAF LINDEN NAMED 'NORBERT'

[76] Inventor: Willet N. Wandell, Rte. #1, Box 286, Oquawka, Ill. 16469

[21] Appl. No.: 120,494

[22] Filed: Nov. 13, 1987

[51] Int. Cl.[4] ..... A01H 5/00

[52] U.S. Cl. ..... Plt./51

[58] Field of Search ..... Plt./51

*Primary Examiner*—James R. Feyrer

[57] ABSTRACT

A new and novel *Tilia cordata* having exceptionally straight branches, a definite central leader; the tree assuming a more broadly pyramidal shape than other trees of the specie. Growth rate is exceptionally rapid. The fall foliage coloration is yellow.

10 Drawing Sheets

This new variety of little-leaf linden was discovered by me growing on cultivated property in Green Bay, Wis. The new variety has a tight, dense pyramidal crown with a straight single leader and maintains this neat appearance with age. The branches are strongly ascending, not two-ranked, forming a symmetrical limb scaffold laterally around the trunk that is easy to structure in the nursery. The leaves are bright green, shiny, leathery and are moderately resistant to aphid colonization. The leaves and buds are much closer together on lateral branches resulting in a higher leaf population than the species or other observed cultivars. Young plants propagated by budding grow rapidly with the trunk diameter increasing nearly twice as much as the species or other observed cultivars. I have approximately 150 asexually produced trees in my nursery, all of which exhibit the superior qualities of the parent plant. Asexual reproduction, by budding, has been performed by me and under my direction.

SUMMARY OF INVENTION

A new and distinct variety of littleleaf linden characterized by the tight, dense pyramidal crown, straight single leader, neat appearance at maturity, strongly ascending branches that form a symmetrical limb scaffold laterally around the trunk rather than the common two-ranked limb dispersion commonly found in littleleaf lindens, unique bright green, shiny, leathery foliage that demonstrates moderate resistance to aphid infestation, close spacing of leaves and buds on lateral branches and a rapid growth rate with the trunk diameter increasing nearly twice as much as the species or other observed cultivars.

DESCRIPTION OF THE NEW PLANT

Figure 1:
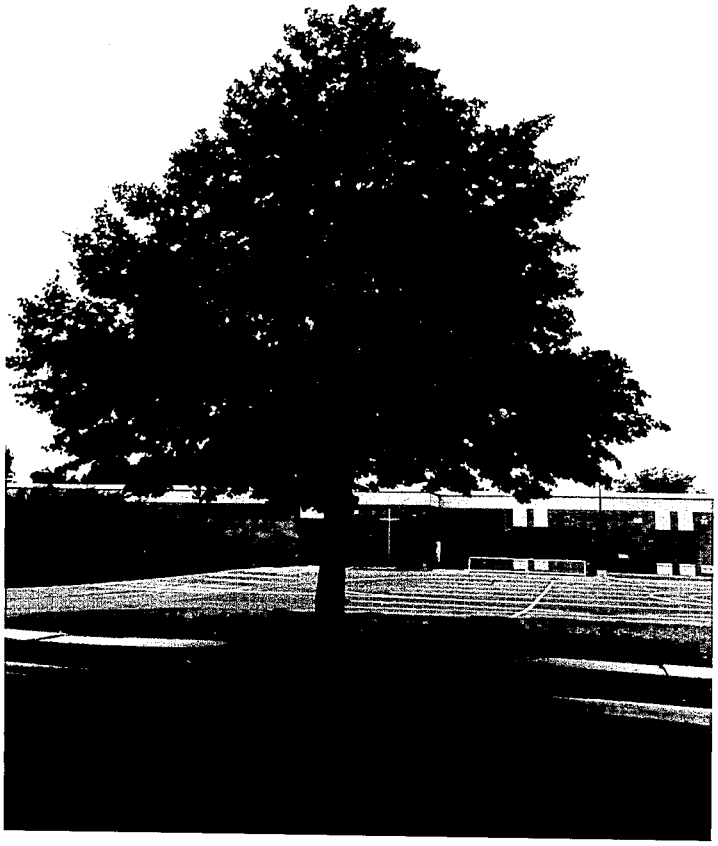
FIG. 1 is a photographic view of the mature tree in leaf.
Figure 2:
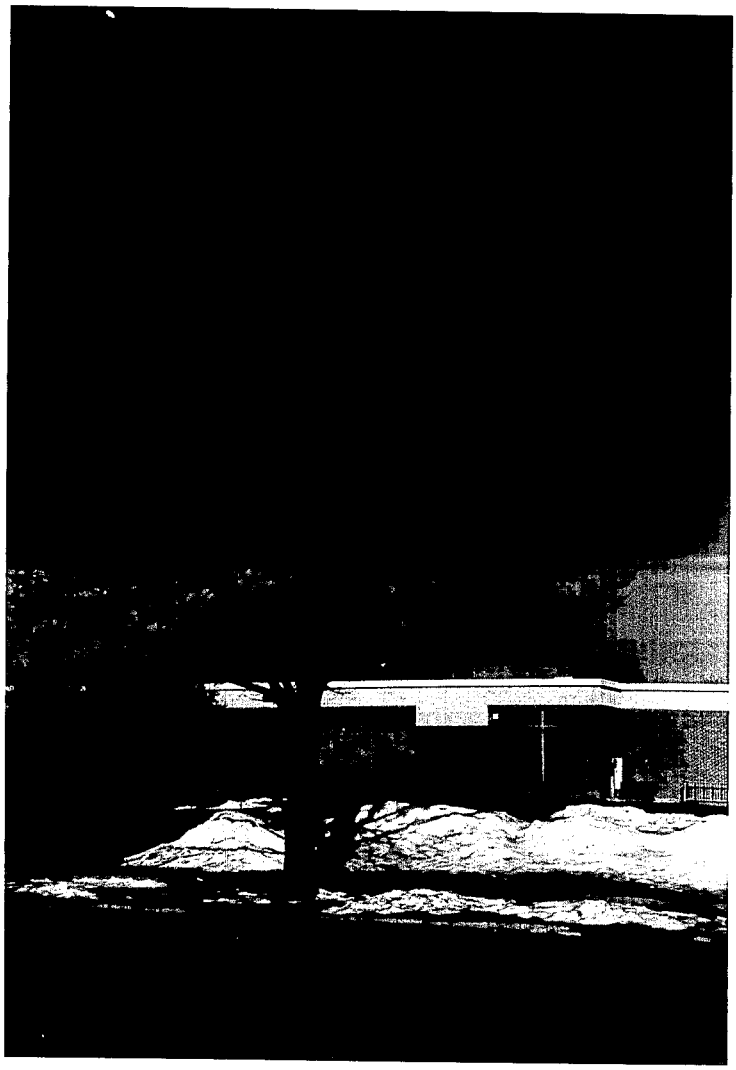
FIG. 2 is a photographic view of the dormant tree.
Figure 3:
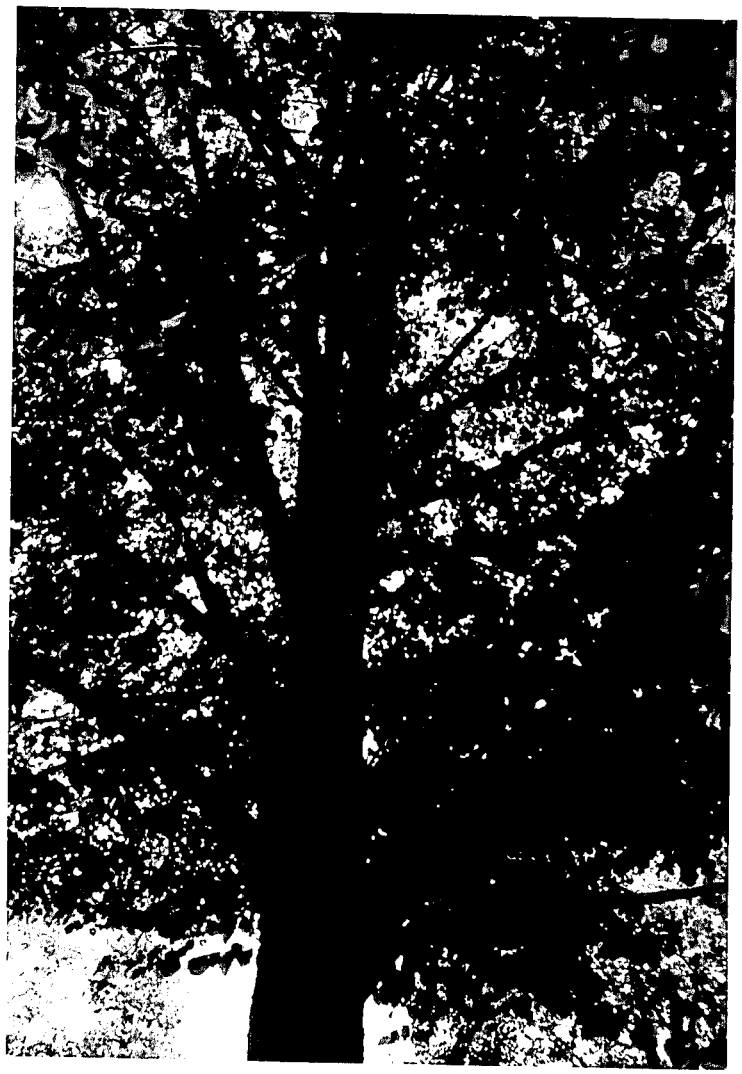
FIG. 3 is a photographic view of the interior crown of the tree showing the symmetrical limb scaffold and dense crown.
Figure 4:
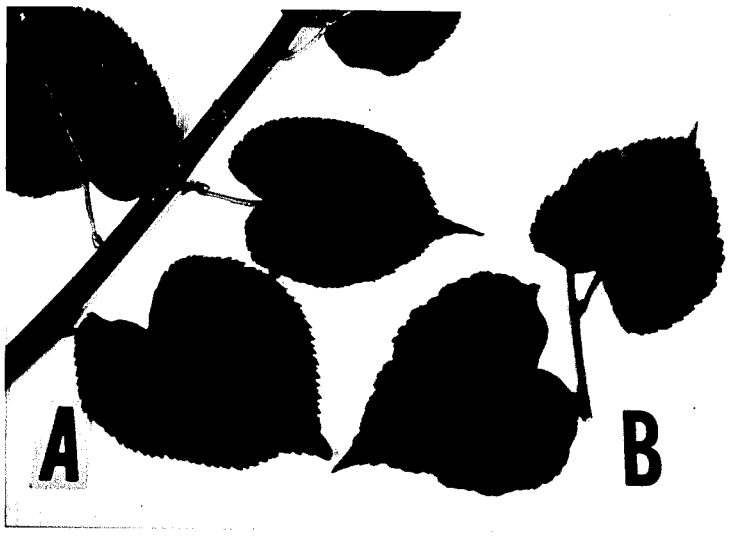
FIG. 4 is a photographic view of the foliage of my new variety (Example "A") compared to seedling littleleaf linden (Example "B").
Figure 5:
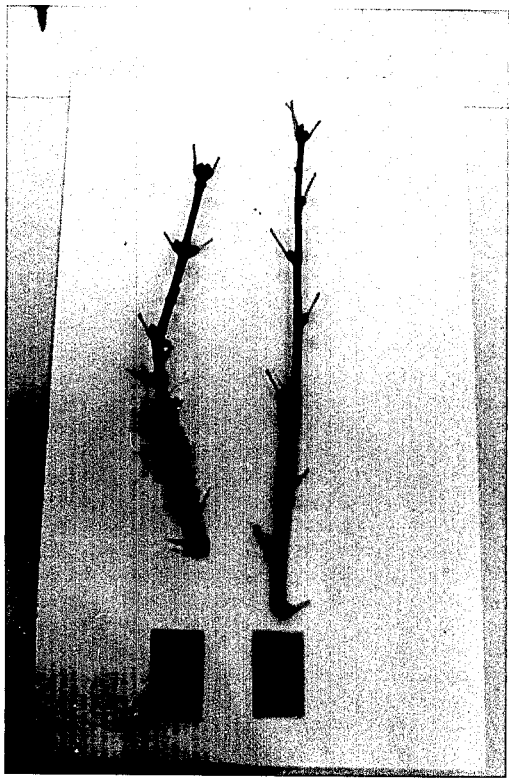
FIG. 5 is a photographic view of the close spacing of the buds on the lateral branches of my new variety (Example "A") compared to another littleleaf linden cultivar (Example "B").
Figure 6:
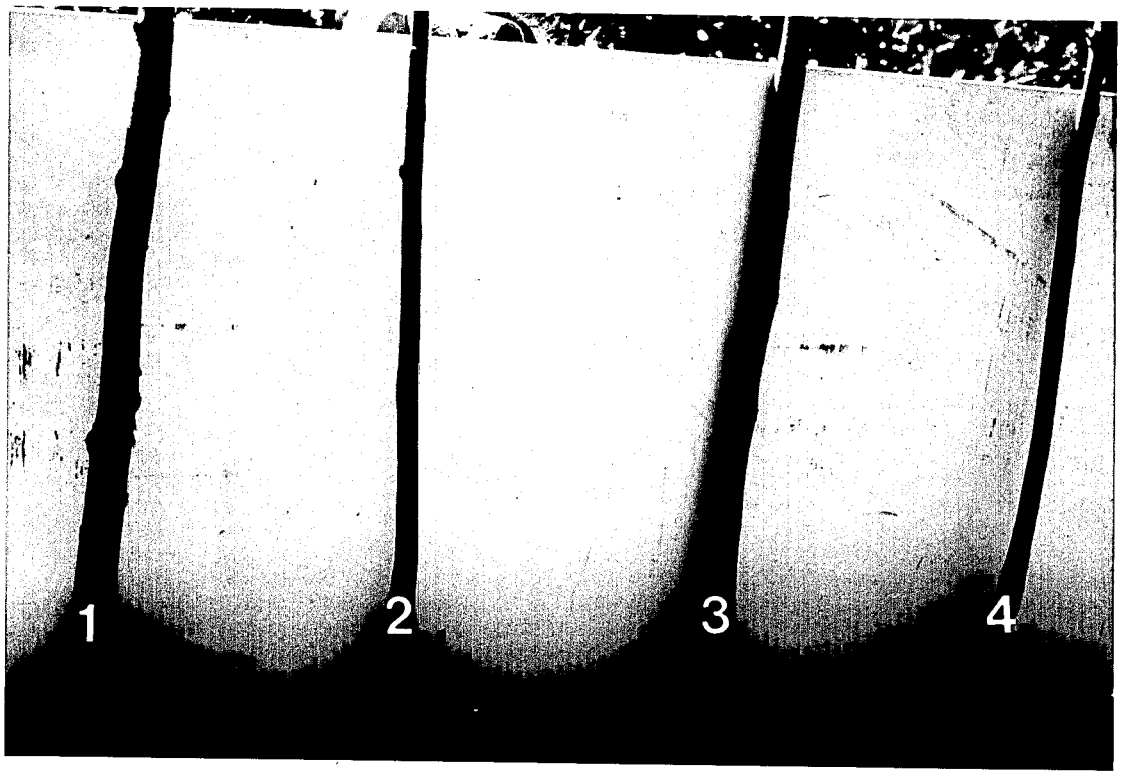
FIG. 6 is a photographic view showing the rapid caliper development of my new variety (Example "1" and "3") compared to another littleleaf linden cultivar (Example "2" and "4").
Figure 7:
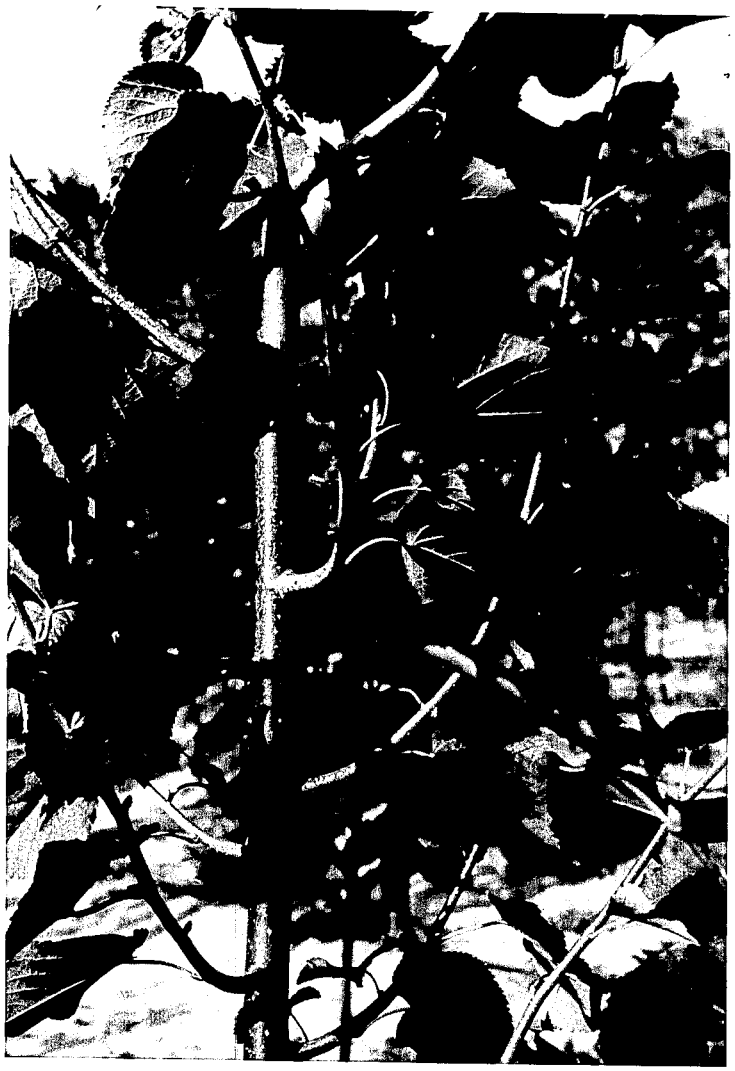
FIG. 7 is a photographic view of the symmetrical limb scaffold laterally developed around the trunk of my new variety.
Figure 8:
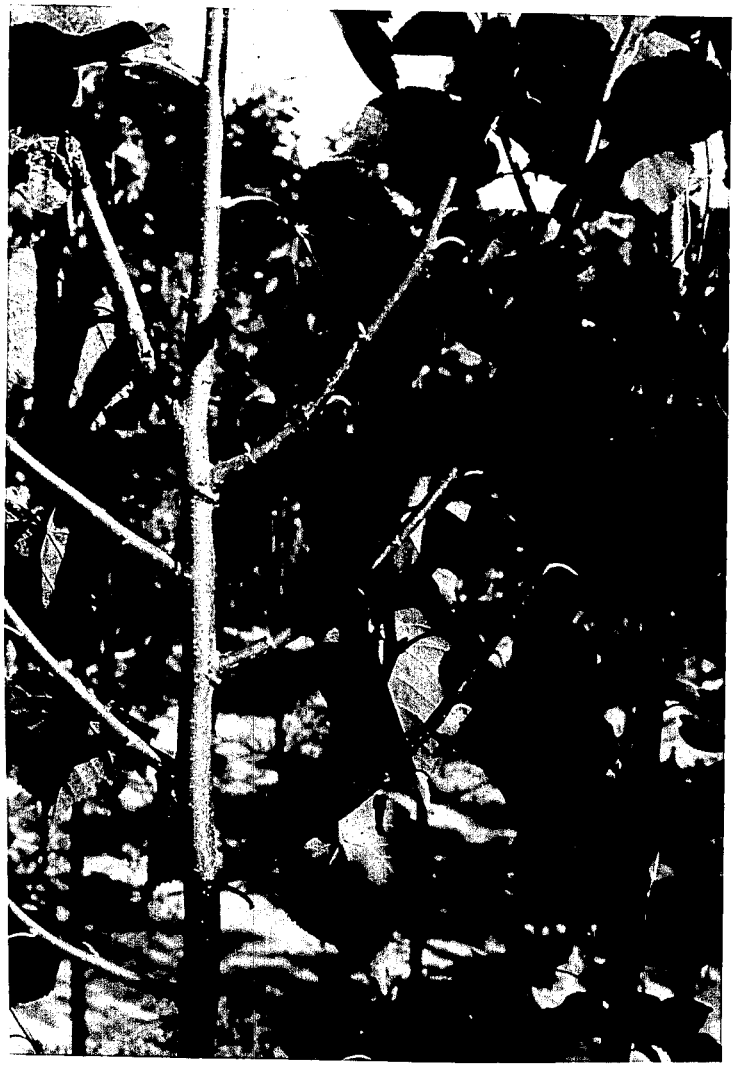
FIG. 8 is a photographic view of the typical two-ranked limb scaffold commonly found in littleleaf lindens.
Figure 9:
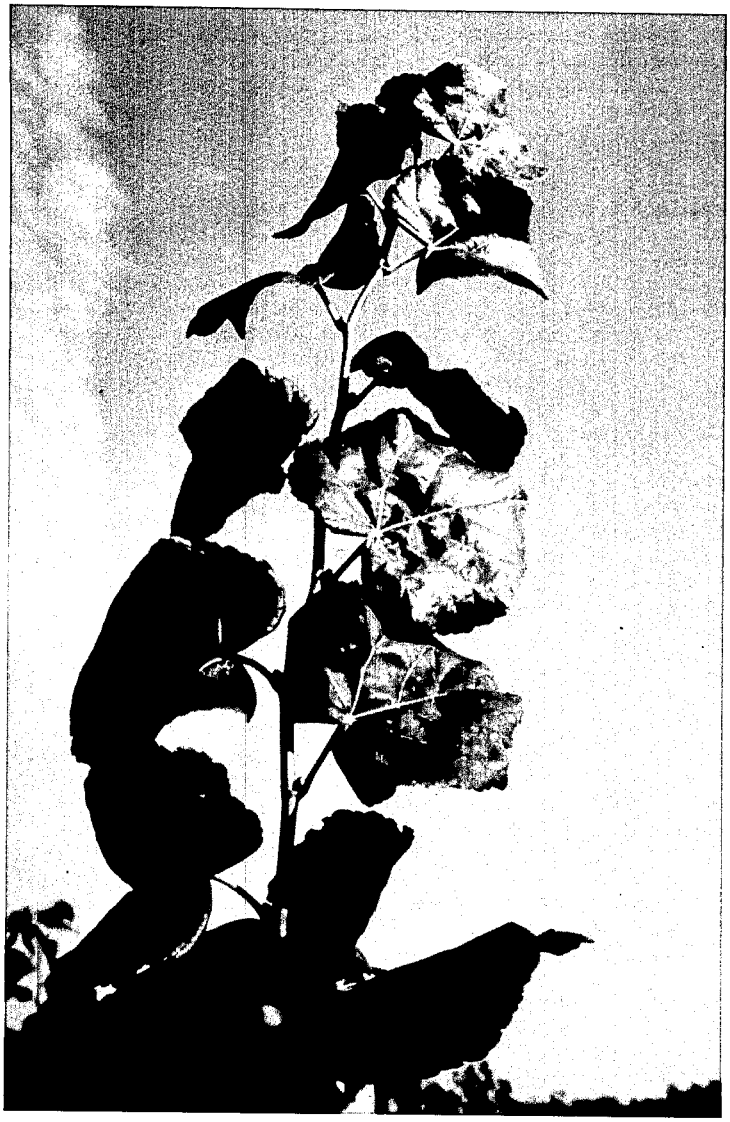
FIG. 9 is a photographic view of the upper surface of the leaf.
Figure 10:
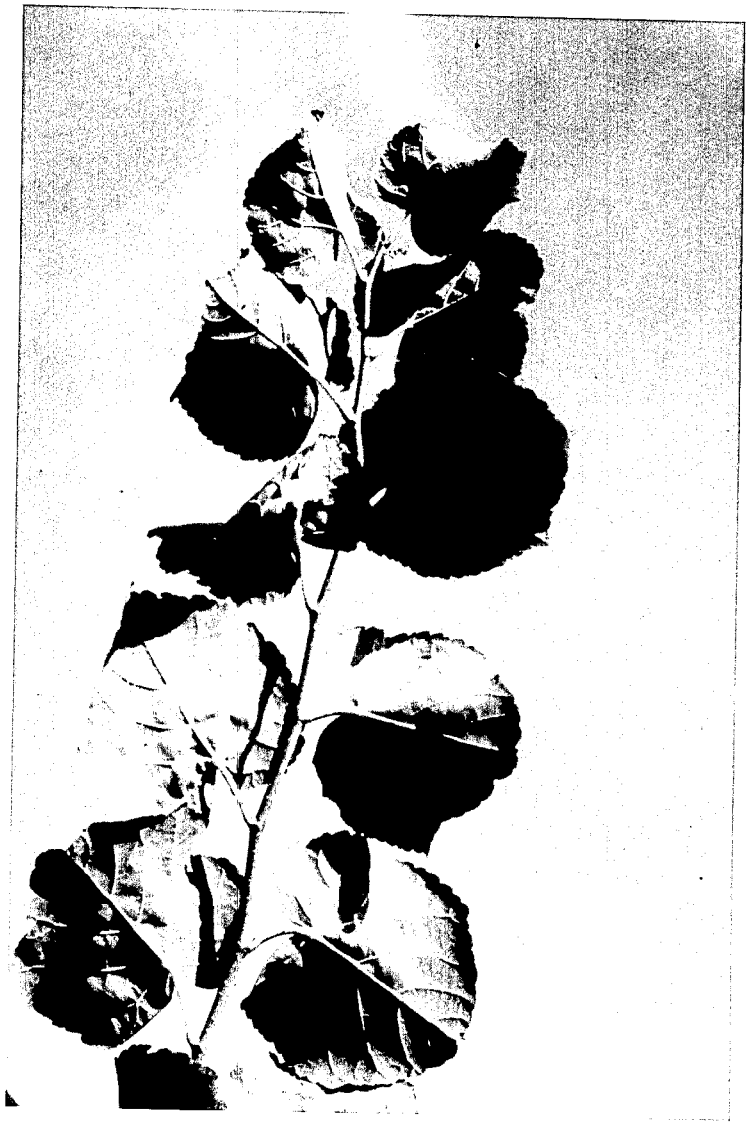
FIG. 10 is a photographic view of the undersurface of the leaf.
Figure 11:
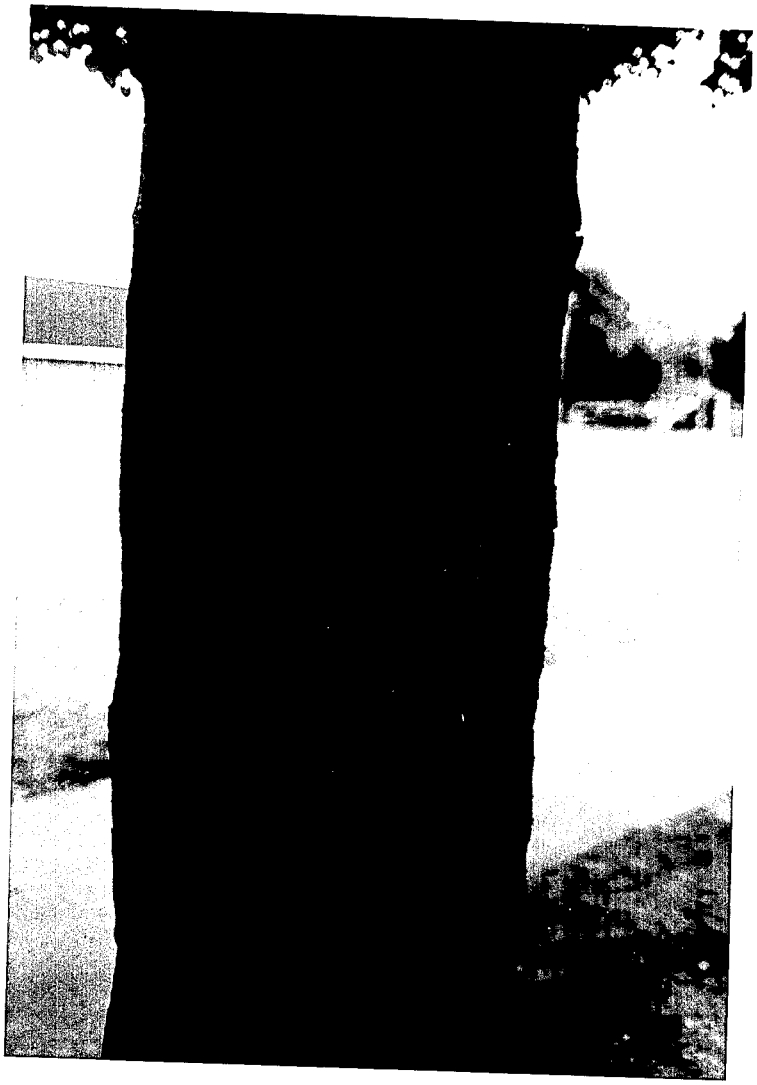
FIG. 11 is a photographic view of the bark of the mature tree.
Figure 12:
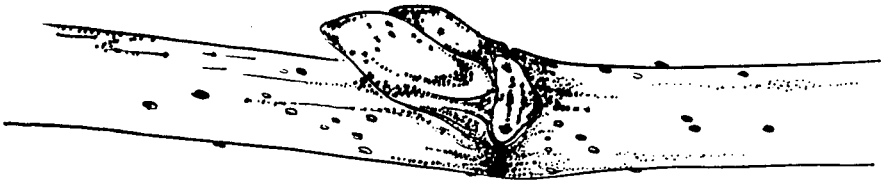
FIG. 12 is a drawing of the leaf scar.

The following is a detailed description of my new variety with color designations according to the R.H.S. Colour Chart published by The Royal Horticultural Society of London, England and the stated observations having been made at Green Bay, Wis. and Oquawka, Ill., by applicant.

Origin: Seedling.

Parentage: A tree of unknown origin and planted in an urban site.

Propagation: Maintains its distinguishing characteristics when propagated by budding.

Classification: *Tilia cordata* var. 'Wandell'.

Form: Medium sized tree.

Habit: A tree with a single trunk, a straight single leader and strongly ascending branches; crown shape densly pyramidal; lateral branches not two ranked, but symmetrically spaced laterally around the trunk.

Growth rate: Rapid.

Bark: Very smooth and light gray on young trees, becoming dark gray with numerous vertical, rather shallow brown fissures.

Leaves: Alternate, simple, deciduous, petiolate, leathery, more or less circular in overall shape with abruptly acuminate apices and symmetrical or slightly asymmetrical cordate bases the margins finely and sharply serrate 9 cm long and 8 cm wide; bright green and shiny above (R.H.S. 139A), pale beneath (R.H.S. 191A); glabrous above and below except for tubes of pale hairs in the vein axils on the lower surface; becoming yellow in the fall.

Winter buds: Solitary, ovoid, glabrous, reddish-brown, with 4 exposed bud scales; borne close together, 2.5–5 mm apart on first year stems.

Twigs: Moderately stout, straight, not zig-zagged, with first year stems to 4.5 mm in diameter, mohogany-red, glabrous, with raised elliptical or circular, beige lenticels; older twigs olive-brown. Leaf scars alternate, half-elliptical, slightly raised, with 3 bundle traces.

Fruit: Nut-like, ellipsoidal, apiculate, densely pubescent with very fine hairs, borne in clusters on bracts.

Flowers: Yellowish-white, borne in 5–9 flowered cymes on pendulous to somewhat upright glabrous bracts; sepals 5, distinct, cymbiform, 3.5–4 mm long, adaxially glabrous except for a few stellate trichomes at the tip, abaxially puberulent at the tip and sericeous at the base; petals 5, elliptical in shape, 4.5–5 mm long, the tips entire or minutely toothed, glabrous; staminodes absent; stamens numerous, about equalling the petals, grouped in fascicles; gynoecium of one compound pistil, 3 mm tall, the ovary pubescent.

I claim:

1. A new variety of the parts thereof, of *Tilia cordata* named 'Norbert', as described and shown herein, that differs from other varieties by the unique combination of: (1) a tight, dense pyramidal crown with a straight single leader and maintaining this neat appearance with age; (2) strongly ascending branches, not two-ranked but forming a symmetrical limb scaffold laterally around the trunk; (3) bright green, shiny, leathery leaves that are moderately resistant to aphid colonization; (4) the close spacing of the leaves and buds on the lateral branches; and (5) rapid rate of growth with the trunk diameter increasing nearly twice as much as the species or other observed cultivars on young plants propagated by budding.

* * * * *